United States Patent
Quinn (10) Patent No.: US 10,390,759 B2
(45) Date of Patent: Aug. 27, 2019

(54) PHYSICAL ASSESSMENT PARAMETER MEASURING DEVICE

(71) Applicant: Welch Allyn, Inc., Skaneateles Falls, NY (US)

(72) Inventor: David E. Quinn, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 429 days.

(21) Appl. No.: 15/053,661

(22) Filed: Feb. 25, 2016

(65) Prior Publication Data

US 2017/0245797 A1    Aug. 31, 2017

(51) Int. Cl.
*A61B 5/00* (2006.01)
*A61B 5/01* (2006.01)

(52) U.S. Cl.
CPC ............ *A61B 5/6833* (2013.01); *A61B 5/002* (2013.01); *A61B 5/6846* (2013.01); *A61B 2562/164* (2013.01)

(58) Field of Classification Search
CPC ........... A61B 5/00; A61B 5/01; A61B 5/0205; A61B 5/002; A61B 5/6833; A61B 5/0008; A61B 5/742; A61B 5/02055; A61B 2562/0271
USPC ........................................................ 600/300
See application file for complete search history.

(56) References Cited

U.S. PATENT DOCUMENTS

| 5,263,481 | A | 11/1993 | Axelgaard |
| 5,948,006 | A | 9/1999 | Mann |
| 6,275,737 | B1 | 8/2001 | Mann |
| 7,206,630 | B1 | 4/2007 | Tarler |
| 8,930,147 | B2 * | 1/2015 | Pollack ............... A61B 5/0008 702/19 |
| 9,014,778 | B2 | 4/2015 | Datta et al. |
| 9,669,231 | B1 * | 6/2017 | Clark ..................... A61N 5/025 |
| 2010/0036369 | A1 | 2/2010 | Hancock |
| 2011/0237922 | A1 | 9/2011 | Parker, III et al. |
| 2012/0029309 | A1 | 2/2012 | Paquet et al. |
| 2013/0018249 | A1 | 1/2013 | Storm |
| 2013/0277435 | A1 | 10/2013 | Bielmann et al. |
| 2014/0121557 | A1 | 5/2014 | Gannon et al. |
| 2014/0371802 | A1 | 12/2014 | Mashiach et al. |
| 2015/0073231 | A1 | 3/2015 | Beck et al. |
| 2017/0215729 | A1 * | 8/2017 | Mullin .................. A61B 5/002 |

FOREIGN PATENT DOCUMENTS

| CN | 102610534 A | 7/2012 |
| WO | 2011081891 A1 | 7/2011 |

OTHER PUBLICATIONS

Hemanshu K Chawda & Zi Ling Kang, "Wireless Pulse Rate Monitoring using Near Field Communication", May 2008.

* cited by examiner

*Primary Examiner* — Jon Eric C Morales
(74) *Attorney, Agent, or Firm* — Merchant & Gould P.C.

(57) ABSTRACT

A physical assessment parameter sensing device includes a layer attachable to a patient, a sensing unit operable to detect a physical assessment parameter of the patient, and an antenna connected to the circuit and operable to receive and transmit a radio frequency signal. The antenna is movably disposed within the sensing device. In certain examples, the sensing device includes an enclosure within which the antenna is movably received.

16 Claims, 9 Drawing Sheets

PHYSICAL ASSESSMENT PARAMETER MEASURING DEVICE

BACKGROUND

Wearable body sensors can be used to efficiently monitor physiological parameters or vital signs in various situations. For example, when a body temperature needs to be monitored periodically, the patient can wear or carry a thermometer device which can wirelessly communicate with a reading device independent from the thermometer device.

As more data is collected about a patient, more devices may need to be affixed to the patient's body for potentially longer periods of time. In such scenarios, the resiliency and comfort demands of such devices may be implicated.

SUMMARY

In general terms, this disclosure is directed to a physical assessment parameter measuring device. In one possible configuration and by non-limiting example, the device is configured as a patch including one or more non-stretchable components that are at least partially movable within the patch. Various aspects are described in this disclosure, which include, but are not limited to, the following aspects.

One aspect is a physical assessment parameter sensing patch including a first layer, a circuit and an antenna. The first layer includes an adhesive configured to be removably applied to a surface of a subject. The circuit is fixed relative to the first layer and includes a sensor unit and a communication unit. The sensor unit is operable to detect one or more physical assessment parameters of the subject. The communication unit is configured to wirelessly communicate with a reading device. The antenna is electrically connected to the communication unit and configured to receive and transmit a radio frequency signal. The antenna is movably disposed within the sensing patch relative to the first layer.

Another aspect is a system for detecting a physical assessment parameter of a subject. The system includes a sensing patch and a reading device. The sensing patch includes a first layer, a circuit, and an antenna. The first layer includes an adhesive configured to be removably applied to a surface of the subject. The circuit is fixed relative to the first layer and includes a sensor unit. The sensor unit is operable to detect one or more physical assessment parameters of the subject. The antenna is electrically connected to the circuit and configured to receive and transmit a radio frequency signal. The antenna is movably disposed within the sensing patch relative to the first layer. The reading device is configured to communicate with the sensing patch and receive the one or more physical assessment parameters from the sensing patch.

DETAILED DESCRIPTION

Various embodiments will be described in detail with reference to the drawings, wherein like reference numerals represent like parts and assemblies throughout the several views.

In general, a physical assessment parameter sensing device in accordance with an exemplary embodiment of the present disclosure includes an enclosure within which one or more rigid components, such as an antenna, is movably received. In some examples, the sensing device of the present disclosure is configured as a patch that can be removably attached to a surface (e.g., skin) of a subject (e.g., patient). The antenna enclosure of the sensing patch is sized to enable the rigid components to freely move therewithin. The enclosure is configured to reduce the fixed area or point of the rigid components within the sensing patch. While the patch includes one or more layers made of flexible materials, the flexibility of the patch can be constrained by the rigid components. The antenna enclosure of the present disclosure allows the rigid components to float relative to at least some of the layers and components of the sensing patch, thereby preventing the rigid components from interfering with the flexibility of the sensing patch. Accordingly, the sensing device of the present disclosure can provide comfort to the patient when the patch is attached to the patient's skin. Further, as the patient moves and the skin stretches or shrinks, the patch can fully conform to such deformation of the skin, and thus does not easily come off from the skin and remains properly attached for an intended period time.

Figure 1:
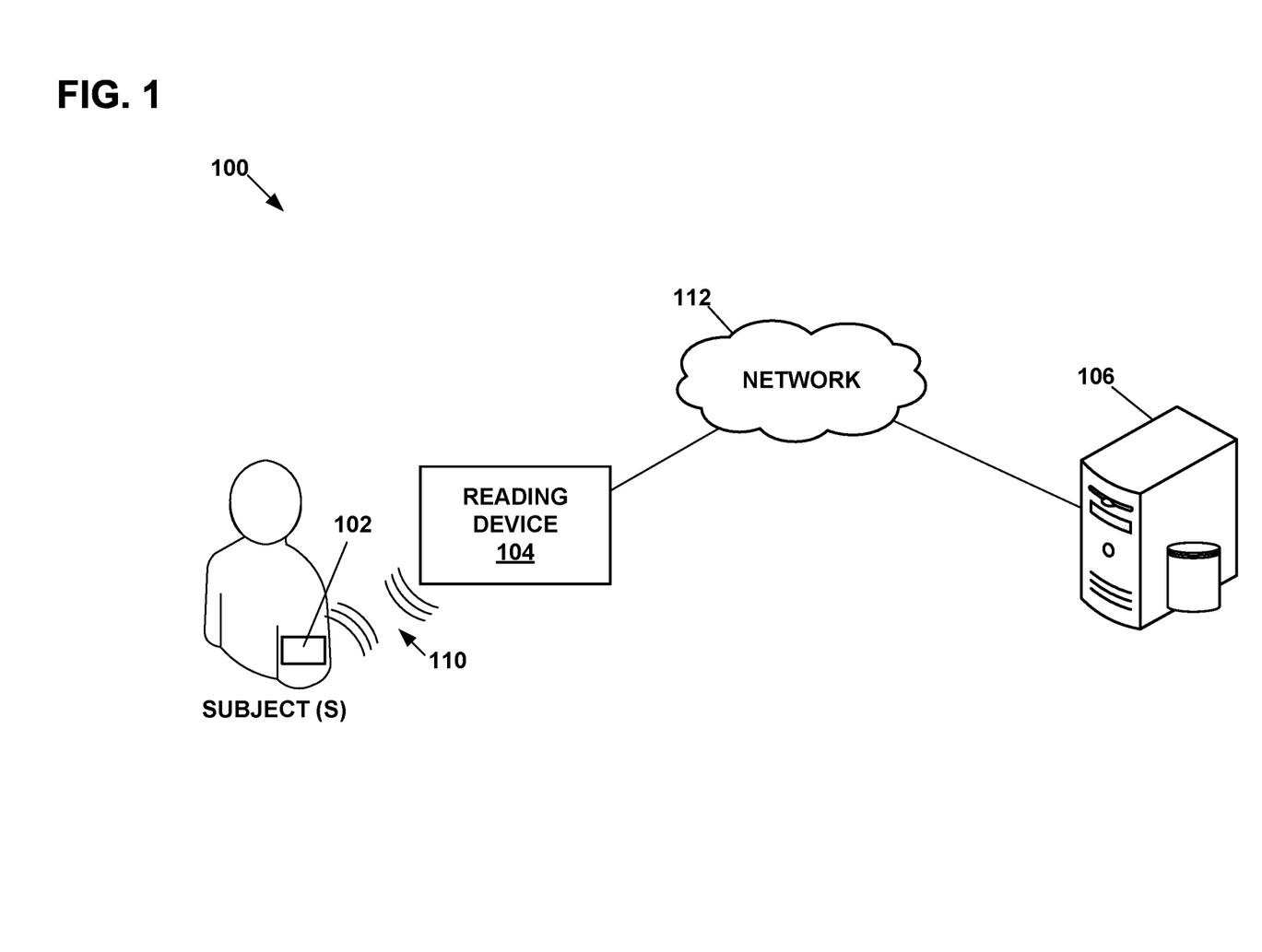
FIG. 1 schematically illustrates an example system for wirelessly sensing one or more physical assessment parameters of a subject.

FIG. 1 schematically illustrates an example system 100 for wirelessly sensing one or more physical assessment parameters of a subject S. The system 100 can include a physical assessment parameter sensing device 102, a reading device 104, and a data management system 106. The physical assessment parameter sensing device 102 can communicate with the reading device 104 via a wireless communication link 110. The reading device 104 can communicate with the data management system 106 via a data communication network 112.

The physical assessment parameter sensing device 102 is worn or carried by the subject S. In some examples, the sensing device 102 includes a physical assessment parameter sensing patch as described below. In this document, therefore, the sensing device 102 is also referred to as a physical assessment parameter sensing patch 102.

In some examples, the sensing device 102 is removably attached to a portion of the subject's body or the subject's skin. The sensing device 102 can be worn on different locations of the subject body, such as the forehead, torso, neck, arm, leg, or other on-body locations, for different measurements. In other examples, the sensing device 102 is implanted to the subject's body. The sensing device 102 can be attached or implanted to the subject S by a healthcare practitioner when the healthcare practitioner sees the subject S. In other examples, the subject S can wear or attach the sensing device 102 on his or her own.

The sensing device 102 operates to detect one or more physical assessment parameters of the subject S. The subject S can also be referred to herein as a patient or person. The sensing device 102 is configured to detect one or more physical assessment parameters. In some examples, the sensing device 102 includes one sensor unit 132 (FIG. 2) to measure the same type of physical assessment parameters. In other examples, the sensing device 102 includes a plurality of sensor units 132 of different types capable of detecting different kinds of physical assessment parameters. The sensing patch 102 transmits signals to the reading device 104 via the wireless communication link 110.

Physical assessment parameters can include vital signs, physiological measurements, and biological measurements, which can be detected from various portions of the subject's body. For example, physical assessment parameters include measurements of the body's basic functions, which are useful in detecting or monitoring medical problems. Examples of physical assessment parameters include body temperature, pulse rate (i.e., heart rate), respiration rate (i.e., breathing rate), and blood pressure. Body temperature can be taken in various manners, such as orally, rectally, by ear, or by skin. The pulse rate is a measurement of the heart rate, or the number of times the heart beats per minute. The pulse rate can also indicate a heart rhythm and the strength of the pulse. The pulse can be taken on different body portions where the arteries are located, such as on the side of the neck, on the side of the elbow, or at the wrist. The respiration rate is the number of breaths a person takes per minute and is used to note whether the person has any difficulty breathing. Blood pressure is the force of the pushing against the artery walls. There may be other vital signs, such as pain, Glasgow coma scale, pulse oximetry, blood glucose level, end-tidal $CO_2$, functional status, shortness of breath, and gait speed.

In some examples, the sensing patch 102 is configured as a passive device, which does not include an independent power source, such as a battery, to supply power to the components of the sensing patch 102. In this configuration, the sensing patch 102 can be activated by the reading device 104 when the reading device 104 comes close to the sensing patch 102 within a predetermined activation or read range. In other examples, the sensing patch 102 is configured as an active device, which includes its own power supply. An example of the sensing device 102 is described and illustrated in more detail with reference to FIGS. 2-8.

With continued reference to FIG. 1, the reading device 104 operates to communicate with the sensing device 102 attached to the subject S. The reading device 104 can receive signals from the sensing patch 102 via the wireless communication link 110. In some examples, the reading device 104 is operable to present the data transmitted from the sensing patch 102 thereon. For example, the reading device 104 includes a display screen and operates to present the transmitted data on the screen in a visible format. The reading device 104 can output the data in an audible format, and/or provide an alert in visible and/or audible manners. The reading device 104 can also be in communication with the data management system 106 via the network 112.

The reading device 104 can be used by a guardian and/or a healthcare practitioner to monitor the measurement of the sensing device 102. The guardian is a person or a group of people who is interested in the health conditions of the subject S. Examples of the guardian include a parent of the subject S, a family member of the subject S, a caregiver of the subject S, a primary physician of the subject S, and any other interested parties. The healthcare practitioner is a person who provides healthcare service to the subject S. Examples of healthcare practitioners P include primary care providers (e.g., doctors, nurse practitioners, and physician assistants), nursing care providers (e.g., nurses), specialty care providers (e.g., professionals in various specialties), and health professionals that provide preventive, curative, promotional and rehabilitative health care services. The healthcare practitioner can be an institution, company, business, and/or entity. In other examples, the reading device 104 can be operated by the subject S him or herself.

The reading device 104 can be of various types. In some examples, the reading device 104 is a computing device dedicated for particular sensing devices 102. In other examples, other consumer level computing devices can be used for the reading device 104. Such computing devices can include a mobile computing device, such as a smartphone, (e.g., an iPhone, an Android operating phone, a Blackberry, a Window operating phone, etc.); a tablet computer (e.g., an iPad), and a personal digital assistant (PDA). The reading device 104 can include a desktop computer, a laptop computer, and/or any other suitable devices operable to send and receive signals, store and retrieve data, and/or execute modules.

In some examples, the reading device 104 is configured a portable reader. Such a portable reading device 104 can be configured as an independent handheld device, or as a device that is connected to a movable clinical data station or equipment. As described herein, for home care, the reading device 104 can be various consumer mobile devices as described above. In other examples, the reading device 104 is mounted to a structure or device that the subject S periodically or continuously uses. For example, the reading device 104 is mounted to the sides or side rails of a hospital or homecare bed for a patient, such that the reading device 104 remains within, or easily comes into, a read range of the sensing patch 102 attached to the patient's body. In yet other examples, the reading device 104 is incorporated into, or used with, other monitoring systems, such as Connex® Vital Signs Monitor (CVSM) available from Welch Allyn Inc., Skaneateles Falls, N.Y. An example of the reading device 104 is described in more detail with reference to FIG. 9.

Referring still to FIG. 1, the data management system 106 operates to manage the subject's health conditions and other information. The subject data management system 108 can be operated by the healthcare practitioner and/or a healthcare service provider, such as a hospital or clinic. Some embodiments of the data management system 106 are configured to receive measurement data (and other data associated with the subject S) from the reading device 104, and analyze the data for various purposes. In some embodiments, the data management system 106 operates to provide information that can be used to assist the guardian and/or the healthcare practitioner to provide suitable healthcare to the subject S. In some examples, the data management system 106 includes such a computing device as described in FIG. 9. Examples of the data management system 106 include Connex® data management systems available from Welch Allyn Inc., Skaneateles Falls, N.Y.

As illustrated in FIG. 1, the wireless communication link 110 is established between the sensing patch 102 and the reading device 104. The data collected by the sensing patch 102 are wirelessly transmitted to the reading device 104 via the wireless communication link 110. The wireless communication link 110 can be established as short range wireless communication, such as radio frequency identification (RFID) communication, near field communication (NFC), Bluetooth communication, or Wi-Fi communication.

In some examples, the reading device 104 is configured as an active RFID reader and capable of communicating with the sensing patch 102, which correspondingly includes a RFID device (e.g., a RFID tag). When the reading device 104 is brought close enough to the sensing patch 102 attached to the subject S, a short-range RF communication is established between the sensing patch 102 and the reading device 104 via electromagnetic fields so that query, authorization/authentication, and/or data interchange processes are performed between the sensing patch 102 and the reading device 104.

In other examples, the reading device 104 includes a NFC interface for establishing radio communication with the sensing patch 102 by bringing the reading device 104 into proximity to the sensing patch 102 or touching the reading device 104 with the sensing patch 102. The NFC interface can be configured in a way known in the art. The sensing device 102 is correspondingly configured to communicate with the NFC interface of the reading device 104. As such, the reading device 104 operates as an NFC reader and the sensing device 102 functions as an NFC tag.

In yet other examples, the reading device 104 includes a Bluetooth communication interface to establish Bluetooth wireless connection with the sensing device 102. The Bluetooth communication interface can be configured in a way known in the art. The sensing device 102 is also configured to be capable of establish Bluetooth communication with the reading device 104. As such, the sensing device 102 and the reading device 104 can be correspondingly configured to transmit data via low-power radio waves.

In yet other examples, the reading device 104 includes a Wi-Fi communication interface to establish Wi-Fi connection with the sensing device 102. The Wi-Fi communication interface can be designed in a way known in the art. The sensing device 102 is also configured to communicate with the Wi-Fi communication interface of the reading device 104. As such, the sensing device 102 and the reading device 104 can be correspondingly configured to transmit data via radio waves. By way of non-limiting example, and as will be appreciated by those skilled in the relevant arts, Wi-Fi can be deployed in accordance with IEEE 802.11 (Wireless LAN), IEEE 802.15.4 (Low-Rate wireless PAN, such as ZigBee, WirelessHART, and MiWi), IEEE 802.22 (Wireless Regional Area Network), or other standard. In some embodiments, Wi-Fi connection can be alternatively established if other connections (e.g., RFID, NFC, and Bluetooth) are not established.

In other embodiments, the wireless communication link 110 can implement other types of short-range communications, such as infrared data communication, Z-Wave, ANT+, and other suitable protocols.

With continued reference to FIG. 1, the data communication network 112 communicates digital data between one or more computing devices, such as among the reading device 104 and the data management system 106. Examples of the network 112 include a local area network and a wide area network, such as the Internet. In some embodiments, the network 112 includes a wireless communication system, a wired communication system, or a combination of wireless and wired communication systems. A wired communication system can transmit data using electrical or optical signals in various possible embodiments. Wireless communication systems typically transmit signals via electromagnetic waves, such as in the form of optical signals or radio frequency (RF) signals. A wireless communication system typically includes an optical or RF transmitter for transmitting optical or RF signals, and an optical or RF receiver for receiving optical or RF signals. Examples of wireless communication systems include Wi-Fi communication devices (such as utilizing wireless routers or wireless access points), cellular communication devices (such as utilizing one or more cellular base stations), and other wireless communication devices.

As such, since the sensing device 102 and the reading device 104 communicate with each other via the wireless communication link 110, the system 100 allows conveniently measuring physical assessment parameters without requiring the patient's involvement. For example, when a patent with the sensing device 102 is in sleep, a user can simply bring the reading device 104 close to the sensing device 102 to activate the sensing device 102 and/or receive the measurements from the sensing device 102 without waking the patient.

Figure 2:
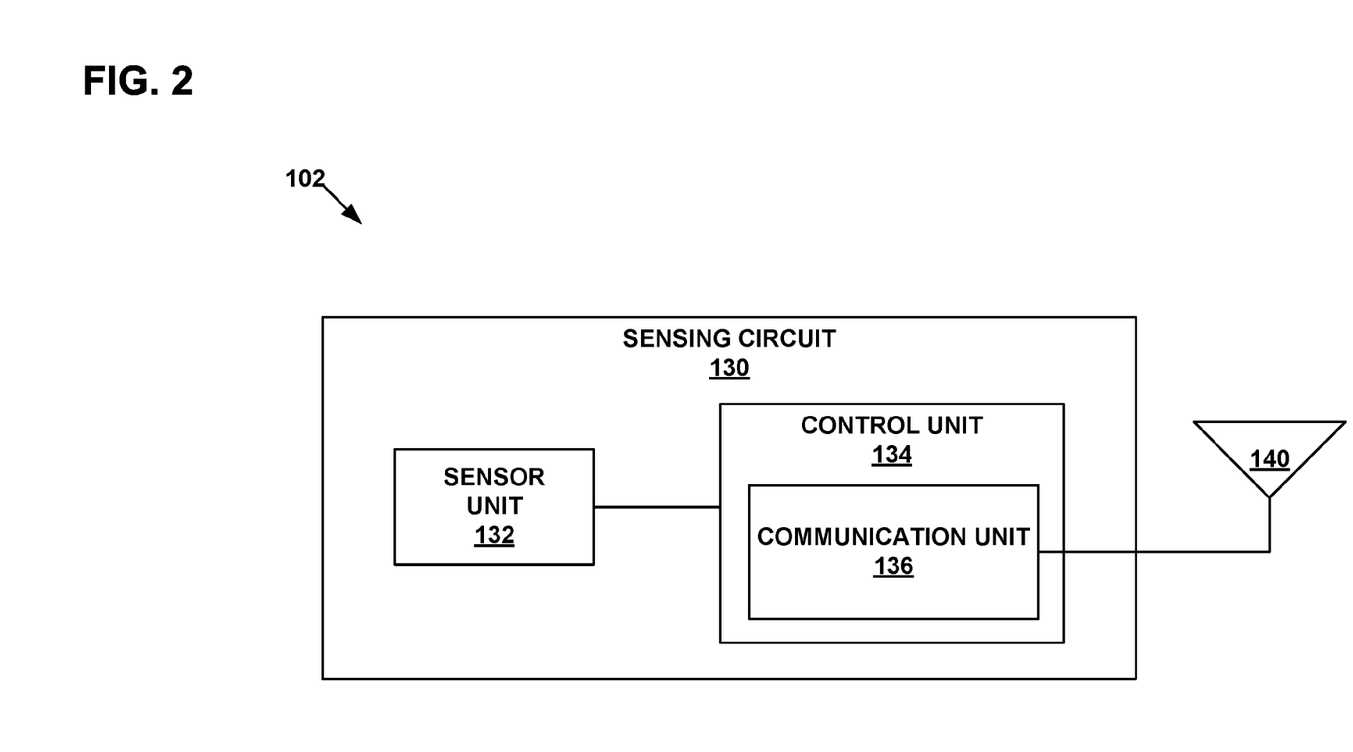
FIG. 2 schematically illustrates an example sensing device for sensing and transmitting physical assessment parameters.

FIG. 2 schematically illustrates an example of the sensing device 102, which is used for sensing and transmitting physical assessment parameters of the subject S. The sensing device 102 includes a sensing circuit 130 and an antenna 140. The sensing circuit 130 can include a sensor unit 132, a control unit 134, and a communication unit 136.

In some embodiments, the sensing device 102 operates as a transponder configured to emit an identifying signal in response to an interrogating received signal. In the depicted example, the sensing device 102 is primarily illustrated as a near field communication (NFC) unit. In other embodiments, the sensing device 102 can be designed to be in other types of communication, such as radio frequency identification (RFID) unit, Bluetooth, Wi-Fi, and other short-range wireless communications.

Figure 4:
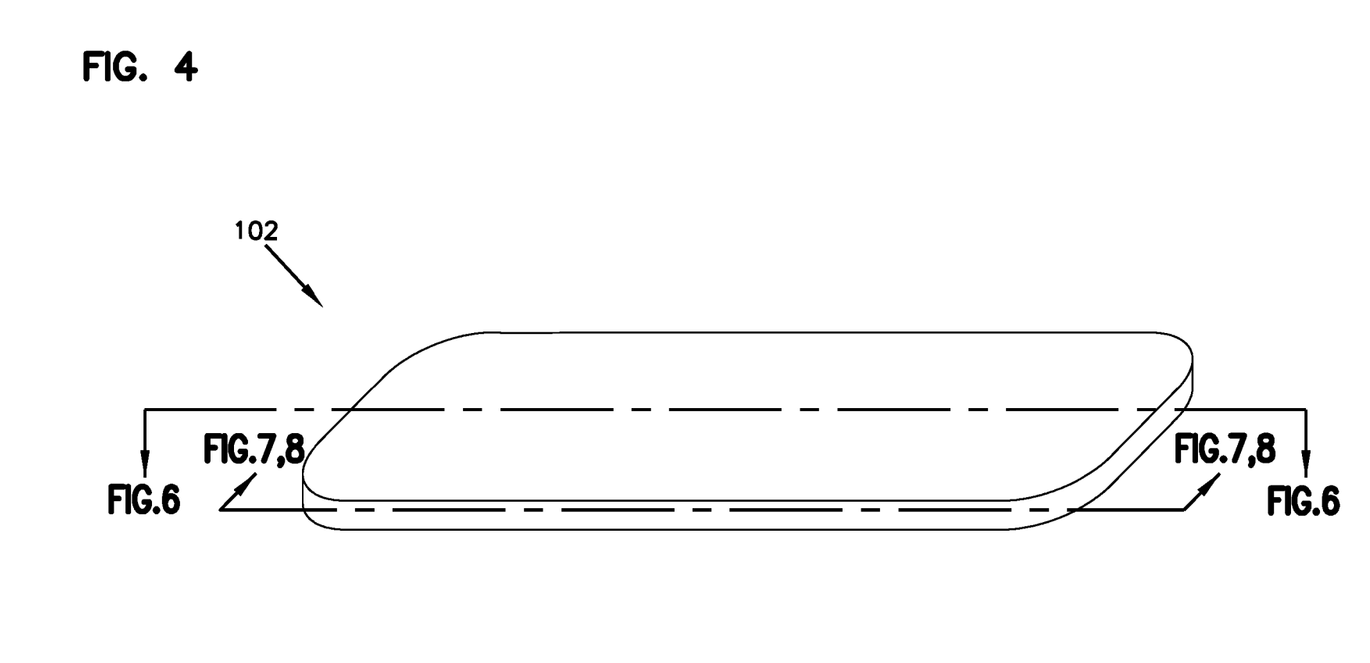
FIG. 4 is a schematic perspective view of the sensing device of FIG. 2
Figure 5:
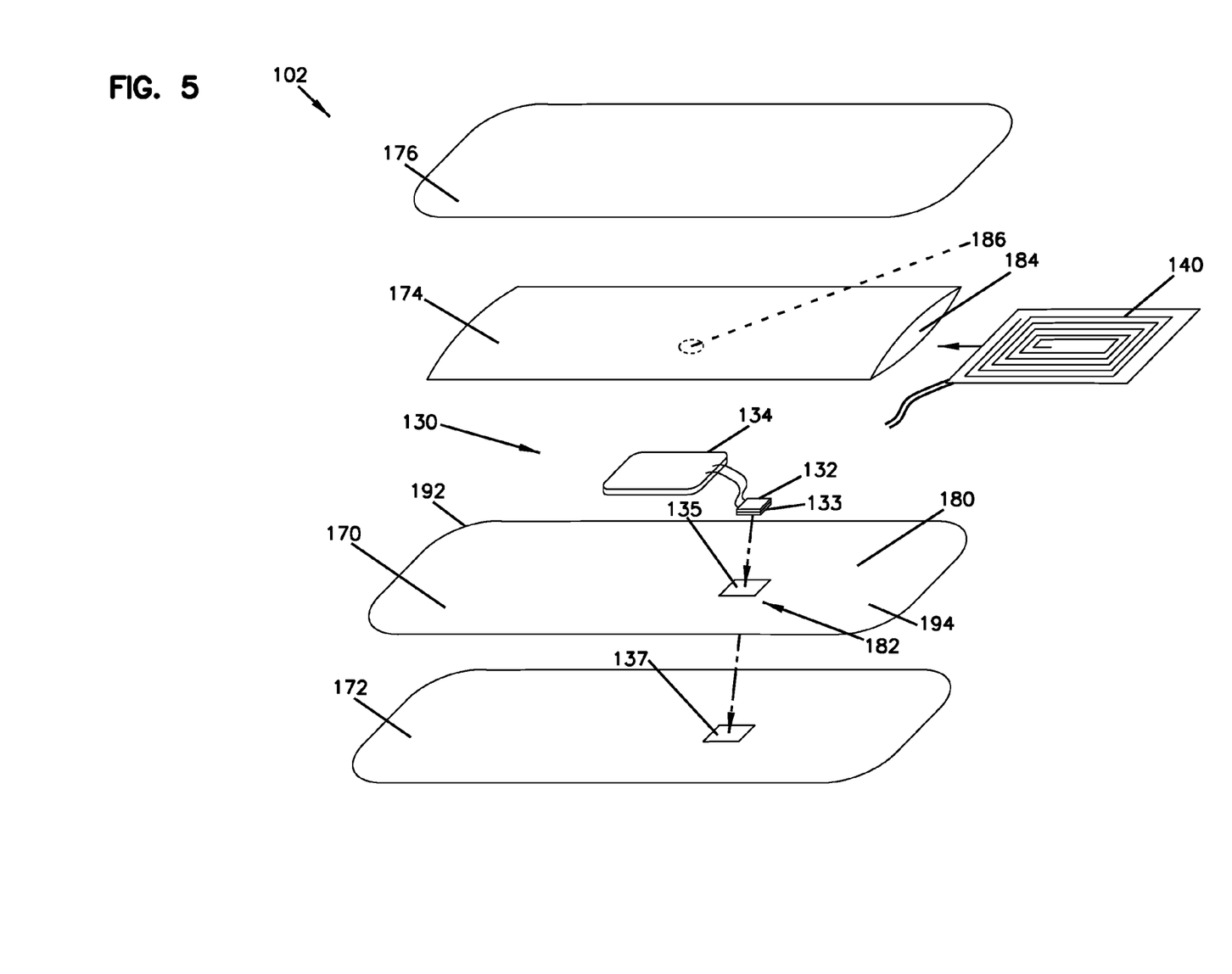
FIG. 5 schematically illustrates example components and layers of the sensing device of FIG. 4.
Figure 6:
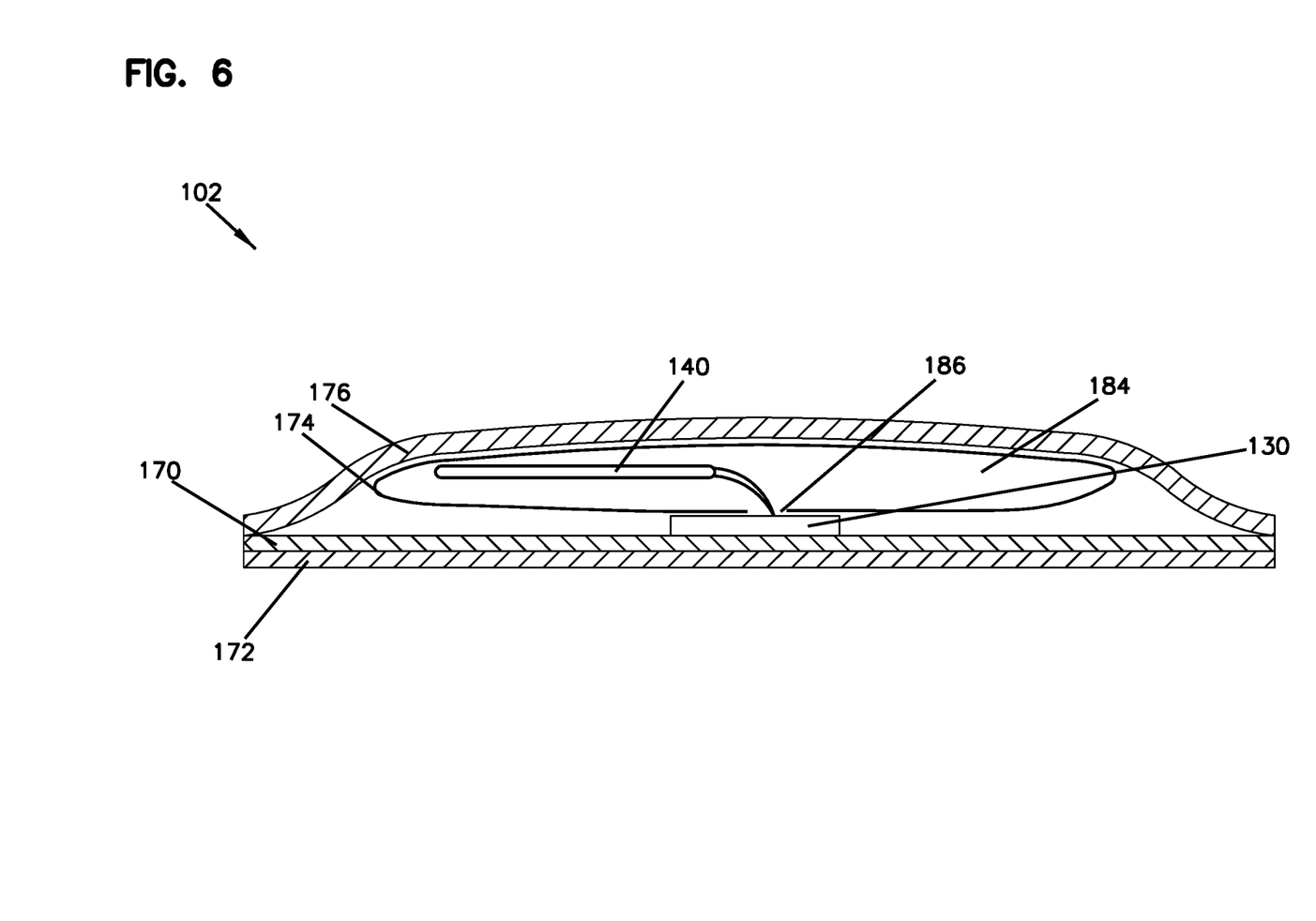
FIG. 6 is a schematic cross-sectional view of the sensing device of FIG. 4.

As further illustrated in FIGS. 4-6, the sensing device 102 can be configured as a patch. The sensing circuit 130 can be designed as a tag or label suitable to be contained within the patch. The tag or label can be formed to be substantially flat and thin so as to be easily mounted onto, or embedded into, the patch.

The sensor unit 132 includes one or more sensors operable to detect one or more physical assessment parameters. In some examples, the sensor unit 132 includes one sensor for detecting one type of physical assessment parameters. In other examples, the sensor unit 132 includes a plurality of sensors for detecting different types of physical assessment parameters. Example sensors of the sensor unit 132 include temperature sensors, heartrate sensors, electrocardiogram (ECG) sensors, respiratory rate sensors, accelerometers, SpO2 sensors, heartrate variability sensors, galvanic skin response sensors, blood pressure sensors, blood glucose sensors, blood oxygen sensors, and any other sensors suitable for measuring physical assessment parameters. The sensor unit 132 can further include one or more sensors (e.g., accelerometer) for detecting the subject's activity and posture, such as whether the subject is standing, sitting, laying down, or engaged in physical activity, such as running.

The control unit 134 operates to process signals obtained by the sensor unit 132. Data processed by the control unit 134 can be stored in a storage unit. An example of the control unit 134 is further described with reference to FIG. 3.

The communication unit 136 operates to send signals obtained by the sensor unit 132 to the reading device 104 via the wireless communication link 110. In some examples, the communication unit 136 can also receive signals from the reading device 104. In some examples, the communication unit 136 is configured to communicate with the data management system 106 and/or other computing devices via the network 112. Although the communication unit 136 is illustrated to be included in the control unit 134, the communication unit 136 can be configured separately from the control unit 134.

The antenna 140 is configured to receive and transmit a radio frequency (RF) signal. In some embodiments, the antenna 140 is configured for NFC communication. The communication range for NFC communication is generally proportional to the size of the antenna. Therefore, it is desirable to increase the antenna size to improve the reading range of a patient worn sensor (e.g., the sensing patch 102).

In some embodiments, the antenna 140 is made flat so as to be incorporated into the sensing patch 102 as illustrated in FIGS. 4-6. In the illustrated example, the antenna 140 is separate from the sensing circuit 130. Since the antenna 140 need not be formed together with the sensing circuit 130 on a single printed circuit board, the sensing circuit 130 can be made smaller, thereby improving comfort when the sensing patch 102 is attached on the subject's body skin. As described above, the sensing circuit 130 includes the sensor unit 132 that can be separated from the processing unit circuit board (e.g., the control unit 134) such that only the sensor unit 132 contacts the body skin. Since the critical skin contact is limited to the sensor unit, the skin contact area required is further reduced. In other embodiments, the antenna 140 can be formed on the sensing circuit 130. An example of the antenna 140 is described and illustrated in more detail with reference to FIGS. 4-8.

Figure 3:
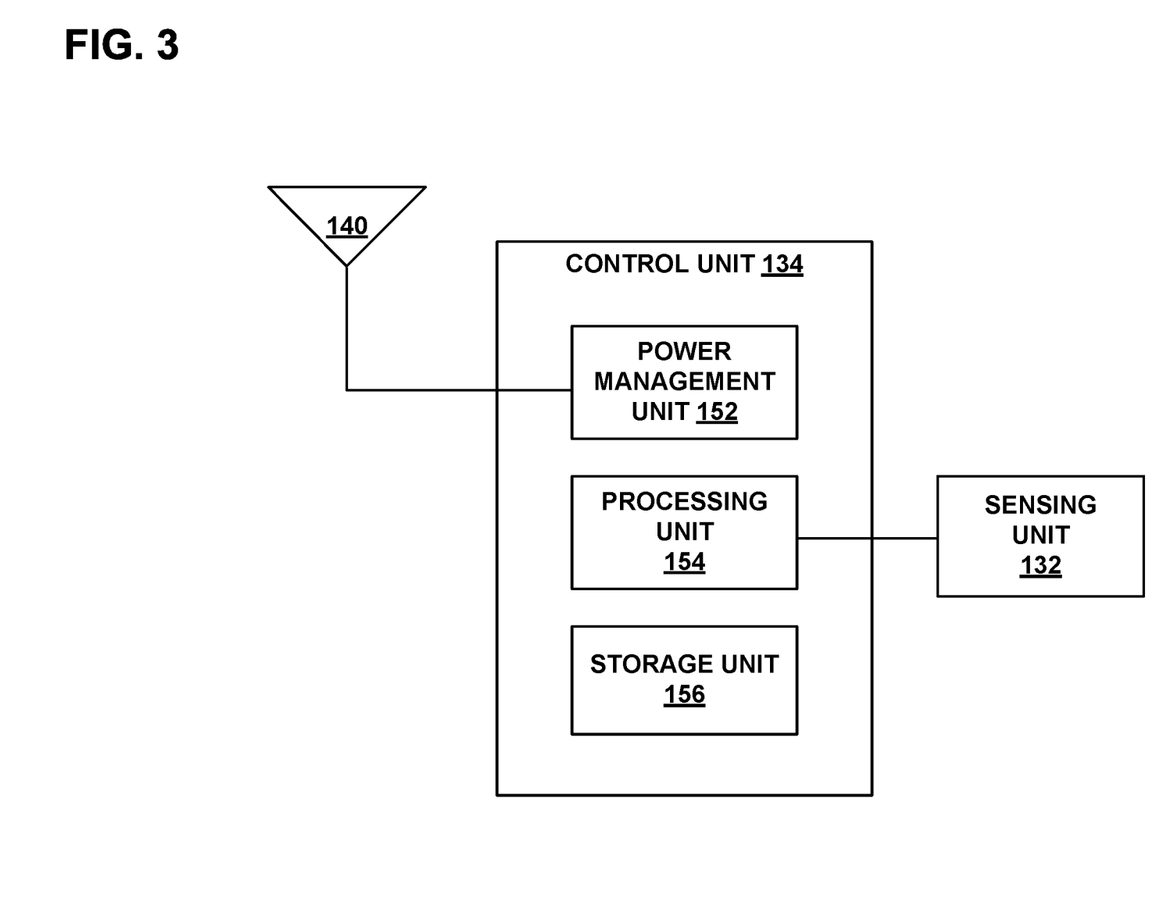
FIG. 3 schematically illustrates an example control unit of the sensing device of FIG. 2.

FIG. 3 schematically illustrates an example of the control unit 134 of FIG. 2. In the illustrated example, the control unit 134 is configured for NFC or RFID communication.

The control unit 134 is arranged within the sensing patch 102 and electrically coupled to the antenna 140. In some embodiments, the control unit 134 is implemented in an integrated circuit (IC). In operation, a signal is received by the antenna 140 and communicated to the control unit 134. The control unit 134 operates to harvest power and respond as necessary in response to the incoming signal. In particular, the control unit 134 is configured to store and process information, modulate and demodulate a RF signal, collect power from an associated reader signal, and perform other functions. One example of the control unit 134 is implemented with model number RF430FRL152H, available from Texas Instruments Inc., Dallas, Tex.

In some embodiments, the control unit 134 includes a power management unit (PMU) 152, a processing unit 154, and a storage unit 156. In other embodiments, the control unit 134 can include one or more components in addition to the components described above, and/or replace one or more of the components described above by different components.

The PMU 152 operates to harvest raw RF power received via the antenna 140. In particular, an RF wave received via the antenna 140 is transmitted to the PMU 152 as a signal. The signal is used for harvesting the power and also decoded for further processes. Where the sensing patch 102 is implemented as a passive NFC device, the sensing patch 102 does not have its own power source. The sensing patch 102 can be powered by electromagnetic induction from magnetic fields produced near a reader of the sensing patch 102 (e.g., the reading device 104). However, it is recognized that the control unit 134 can be powered in different manners. For example, where the sensing patch 102 is implemented as an active or semi-passive RFID tag, the sensing patch 102 uses internal power source to power the circuit.

The processing unit 154 operates to receive signals from the antenna 140. In some examples, a demodulator is provided to demodulate an RF signal received via the antenna 140. The demodulator can be implemented in a way known in the art, including, for example, attenuator stage and amplifier stage. The processing unit 154 can perform various operations and generate an output signal for transmission. In some examples, a modulator is provided to modulate an output signal generated by the processing unit 154. The modulated signal is transmitted through the antenna 140 to one or more readers, such as the reading device 104. The modulator can be implemented in a way known in the art, including, for example, driver stage and amplifier stage. The processing unit 228 can be implemented in a way known in the art, including, for example, a processor, a decoder, and an encoder.

The storage unit 156 includes one or more memories configured to store data readable by a reader, such as the reading device 104. The storage unit 156 can be of various types, including volatile and nonvolatile, removable and non-removable, and/or persistent media. In some embodiments, the storage unit 156 is an erasable programmable read only memory (EPROM).

Referring to FIGS. 4-6, an example structure of the sensing device 102 is described. In particular, FIG. 4 is a schematic perspective view of the sensing device 102. FIG. 5 schematically illustrates example components and layers of the sensing patch 102 of FIG. 4, and FIG. 6 is a schematic cross-sectional view of the sensing patch 102 of FIG. 4.

As illustrated, the sensing device 102 is configured as a patch that can be removably attached to various portions of the subject's body. In some examples, the sensing patch 102 includes a base substrate or layer 170, an adhesive layer 172, an antenna enclosure 174, and a cover layer 176. As described below, the antenna 140 is movably contained within the sensing patch 102, thereby improving the flexibility of the sensing patch 102 that is attached on the subject's body skin.

Referring to FIGS. 5 and 6, the base substrate 170 has a first surface 180 supporting the sensing circuit 130 thereon, and a second surface 182 (opposite to the first surface) configured to, directly or indirectly, engage a portion of the subject's body (e.g., body surface). In some examples, the adhesive layer 172 is provided on the second surface 182 of the base substrate 170 to allow the base substrate 170 (and thus the patch 102) to be attached to a body surface of the subject S. In other examples, the second surface 182 of the base substrate 170 is adapted to be removably attached to a body surface of the subject S with or without the adhesive layer 172. In some examples, the base substrate 170 is made of flexible materials, such as polymeric materials, which are stretchable to remain attached to a body skin when the body skin deforms.

The adhesive layer 172 can be made of various materials. In some examples, the adhesive layer 172 is made of flexible polymeric materials, which are stretchable to conform to the deformation of a body skin on which the sensing patch 102 is attached. The adhesive layer 172 can include a hydrogel, which can provide skin-adhesion properties. The adhesive layer 172 can further function as a thermal conduit between the sensor unit 132 and the subject's skin. In addition or alternatively, the adhesive layer 172 includes a pressure-sensitive adhesive.

In addition or alternatively, the adhesive layer 172 is further configured as an electrically conductive layer that can conduct current between the skin and the circuit. Further, such an electrically conductive layer can also transfer a measurement of a voltage potential between two different points on the patient to the sensing circuit.

In some examples, the base substrate 170 is configured such that the entire second surface 182 of the base substrate 170 is substantially attached to a predetermined body skin of the subject S, either directly or through the adhesive layer 172. In other examples, the base substrate 170 is configured to be attached to a body skin at a limited number of points of the second surface 182 of the base substrate 170 (either directly or via the adhesive layer 172). For example, in the illustrate example, the base substrate 170 can be attached to a body skin at two points adjacent opposite corners 192 and 194 (FIG. 5). This configuration can be used in measuring a stretch of a skin, which, for example, can be used to calculate a breath rate.

In some examples, the sensing circuit 130 is disposed between the base substrate 170 and the antenna enclosure 174. The sensing circuit 130 can be attached to the base substrate 170. For examples, the control unit 134 is fixed to a predetermined location on the first surface 180 of the base substrate 170, and the sensor unit 132 is arranged at a location from which a desired physical assessment parameter can be properly detected when the patch 120 is attached to the subject S. Alternatively, the sensing circuit 130 can be attached to the antenna enclosure 174, or attached to both the base substrate 170 and the antenna enclosure 174. In this example, the sensor unit 132 is illustrated to be separate and extend from the control unit 134. In other examples, the sensor unit 132 can be incorporated with the control unit 134 as a single printed circuit board.

In some embodiments, the sensor unit 132 includes a sensor adhesive layer 133 configured to attach the sensor unit 132 to the subject's skin. The sensor unit 132 can be exposed to the skin through an opening 135 of the base substrate 170 and an opening 137 of the adhesive layer 172.

Where the sensing patch 102 is configured for measuring a body temperature, the sensor unit 132 can include a thermistor in some examples. In other examples, the sensor unit 132 can include other types of electrical temperature sensors.

The antenna enclosure 174 is configured to house the antenna 140 therewithin. The antenna enclosure 174 provides a space or cavity 184 within which the antenna 140 can move. In some examples, the antenna enclosure 174 is configured as a pocket, sleeve, or envelope into which the antenna 140 is received. The antenna enclosure 174 is sized such that the antenna 140 freely moves, or floats, within the antenna enclosure 174. The antenna enclosure 174 can be made from one or more flexible and stretchable materials. The antenna enclosure 174 can be made in other manners. For example, the antenna enclosure 174 can be made by two opposing layers that cooperate together to define a space therebetween. By way of example, such opposing layers can be the base substrate 170 and the cover layer 176.

In some examples, the antenna enclosure 174 includes a wire hole 186 through which electrical wires pass between the antenna 140 and the sensing circuit 130. The electrical wires are used to electrically connect the antenna 140 and the sensing circuit 130.

The cover layer 176 can be disposed above the antenna enclosure 174 and forms an exterior layer of the sensing patch 102. In some examples, the cover layer 176 and the base substrate 170 are connected (e.g., bonded) to each other along their edges to enclose the antenna enclosure 174, the sensing circuit 130, the antenna 140, and other components or layers suitable for the sensing patch 102.

The materials used for the layers of the sensing patch 102 are capable of providing resistance to water, sweat, humidity, and other human or environmental factors that may reduce or deteriorate the bond between the patch 102 and the subject's skin over the length of a predetermined time period.

In some examples, the layers of the sensing patch 102, such as the base substrate 170, the adhesive layer 172, the antenna enclosure 174, and the cover layer 176, are made to be flexible and stretchable to accommodate the movement of a body skin of the subject S to which the sensing patch 102 is attached. As such, when the body skin moves or changes its shape (e.g., the body skin stretches or shrinks), the layers of the sensing patch 102 can remain properly attached to the body skin by conforming to the various shapes of the body skin. Since the sensing circuit 130 is small in size relative to the sensing patch 102, the sensing circuit 130 does not generally interfere with the flexibility of the layers of the sensing patch 102. In other examples, the sensing circuit 130 can also be made with a flexible circuit board so that the layers and the sensing circuit 130 of the sensing patch 102 conform to different shapes of the subject's body skin on which the sensing patch 102 is attached.

In other examples, the sensing patch 102 can include other layers and/or components in addition to all or some of the layers 170, 172, 174 and 176. Further, the layers and components of the sensing patch 102, such as the base substrate 170, the adhesive layer 172, the antenna enclosure 174, the cover layer 176, the sensing circuit 130, the antenna 140, and/or any other layers or components, can be arranged in various manners, different from the order illustrated in FIGS. 5 and 6.

In some examples, the antenna 140 is designed to generally follow the contour of the sensing patch 102. The antenna 140 is made of one or more rigid materials, such as aluminum and copper, which is not stretchable. Where the sensing patch 102 is configured as a NFC or RFID device, the antenna 140 is made from etched metal foil. For example, the antenna 140 can include one or more coils, which are formed as a loop, a spiral, a square or rectangular, on a flat plate.

Several factors can affect a read range between the reading device 104 and the sensing patch 102. One factor is an antenna size. In general, a larger antenna can broadcast farther than a smaller one. However, such a larger antenna interferes more with the flexibility of the sensing patch.

The non-stretchable characteristic and the relatively-large size of the antenna 140 can prevent the sensing patch 102 from confirming to deformation of a body skin and the layers of the sensing patch 102 attached to the body skin and/or restrict natural skin stretching motion. As described above, the antenna enclosure 174 can reduce the interference of the antenna 140 by allowing the antenna 140 to float, or move freely, relative to the sensing patch 102. Therefore, the existence of the antenna 140 does not deteriorate the flexibility of the sensing patch 102, which can thus conform to the deformation of a body skin on which the sensing patch 102 is attached.

Although the sensing patch 102 is made be flexible in general, the sensing patch 102 is configured to be unswallowable and/or not chewable. In some examples, the sensing patch 102 includes one or more layers or members that are at least partially rigid and can thus prevent the subject S (such as a pediatric patient) from accidentally ingesting the sensing patch 102. In other examples, the sensing patch 102 is sized to be large enough so that a pediatric patient is not able to swallow the sensing patch 102. In yet other examples, the sensing patch is treated with a biocompatible, non-toxic coating that has an undesirable taste or flavor to prevent the subject from swallowing or ingesting the patch.

Similarly to the antenna 140 above, in some examples, the sensing circuit 130 can be movably contained within the sensing patch 102. For example, the sensing circuit 130 can be received within the antenna enclosure 174 so that the sensing circuit 130, as well as the antenna 140, freely moves within the antenna enclosure 174. In other examples, another enclosure, similar to the antenna enclosure 174, can be provided to provide a space for the movement of the sensing circuit 130. For reliable measurement, the sensor unit 132 can be fixed within the sensing patch 102 while the control unit 134 of the sensing circuit 130 and/or the antenna 140 are movably disposed within the sensing patch 102.

Figure 7:
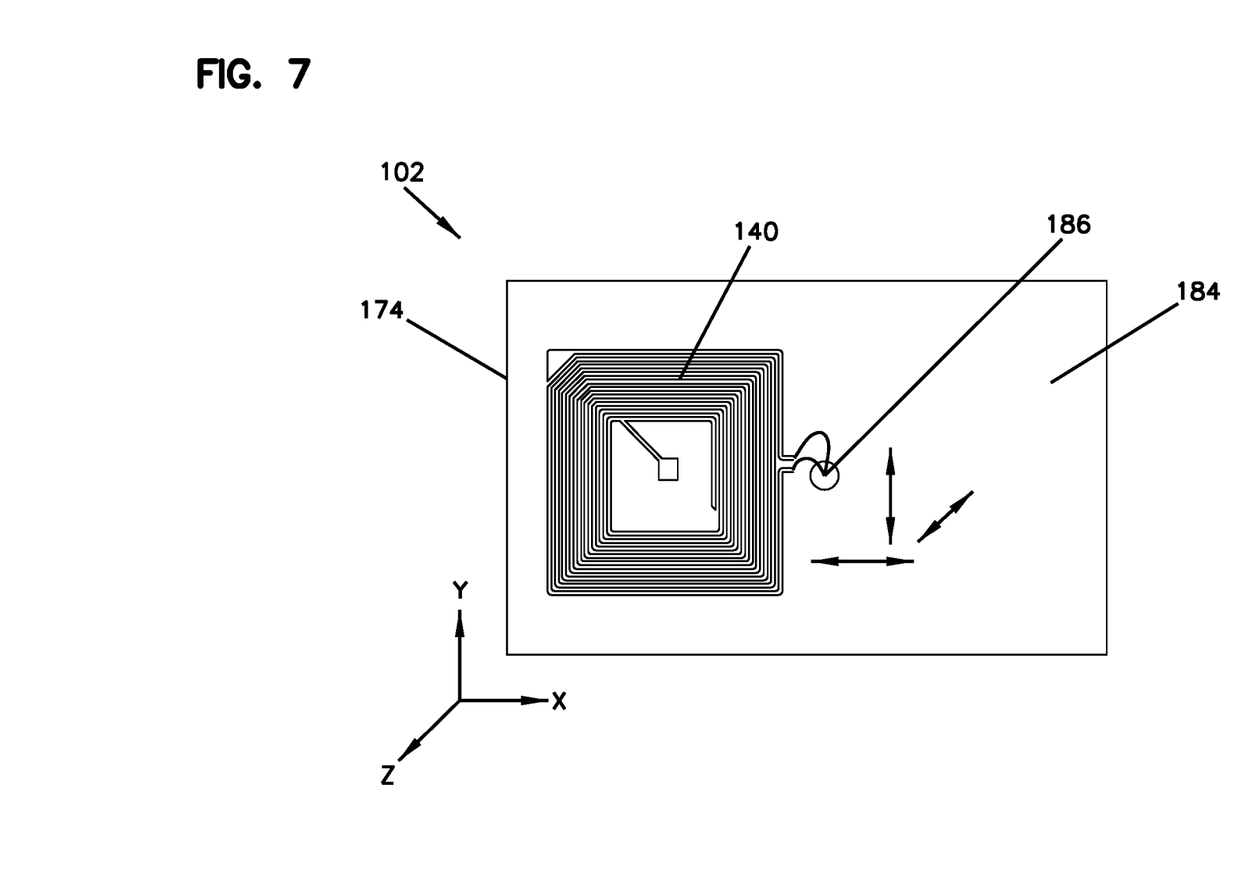
FIG. 7 schematically illustrates an example antenna arrangement within an antenna enclosure of the sensing device.
Figure 8:
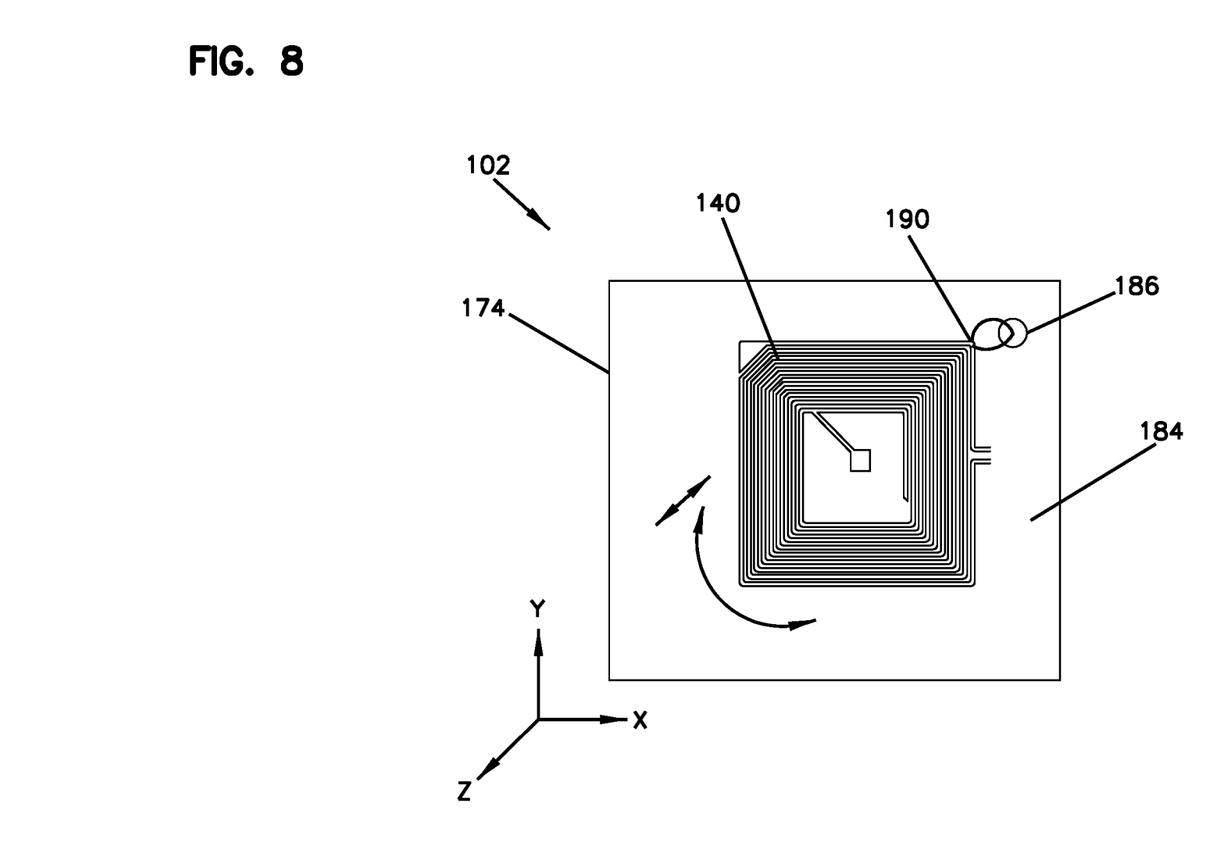
FIG. 8 schematically illustrates another example antenna arrangement within the antenna enclosure of the sensing device.

Referring to FIGS. 7 and 8, the antenna 140 is described to be disposed within the antenna enclosure 174 in various manners. In particular, FIG. 7 schematically illustrates an example arrangement of the antenna 140 within the antenna enclosure 174, and FIG. 8 schematically illustrates another example arrangement of the antenna 140 within the antenna enclosure 174.

With reference to FIG. 7, the antenna 140 is disposed within the antenna enclosure 174 and movable therewithin. The movement of the antenna 140 is only limited by the wires extending from the antenna 140 to the sensing circuit 130 through the wire hole 186. The antenna 140 can freely move in the three-dimensional space of the cavity 184 (e.g., a space defined by three-dimensional Cartesian coordinate system).

With reference to FIG. 8, the antenna 140 can be disposed within the antenna enclosure 174 and pivotally connected at a predetermined anchor point 190. In this configuration, the antenna 140 can pivot about the anchor point 190 on the x-y plane and movable along the z-axis.

The antenna 140 can be fixed at a single point, such as the anchor point 190, and the rest of the antenna 140 is not fixed relative to the subject's skin on which the sensing patch 102 is attached. Therefore, the antenna 140 is allowed to move or slide within the antenna enclosure 174. As such, the sensing patch 102 is not restrained by the rigid antenna 140 and is adapted to be stretchable in response to the deformation (e.g., stretching or shrinking) of the subject's skin. In other examples, the antenna 140 can be fixed at two or more points within the antenna enclosure 174 while the antenna 140 is sufficiently movable within the antenna enclosure 174 as the sensing patch 102 and/or the subject's skin deform.

Figure 9:
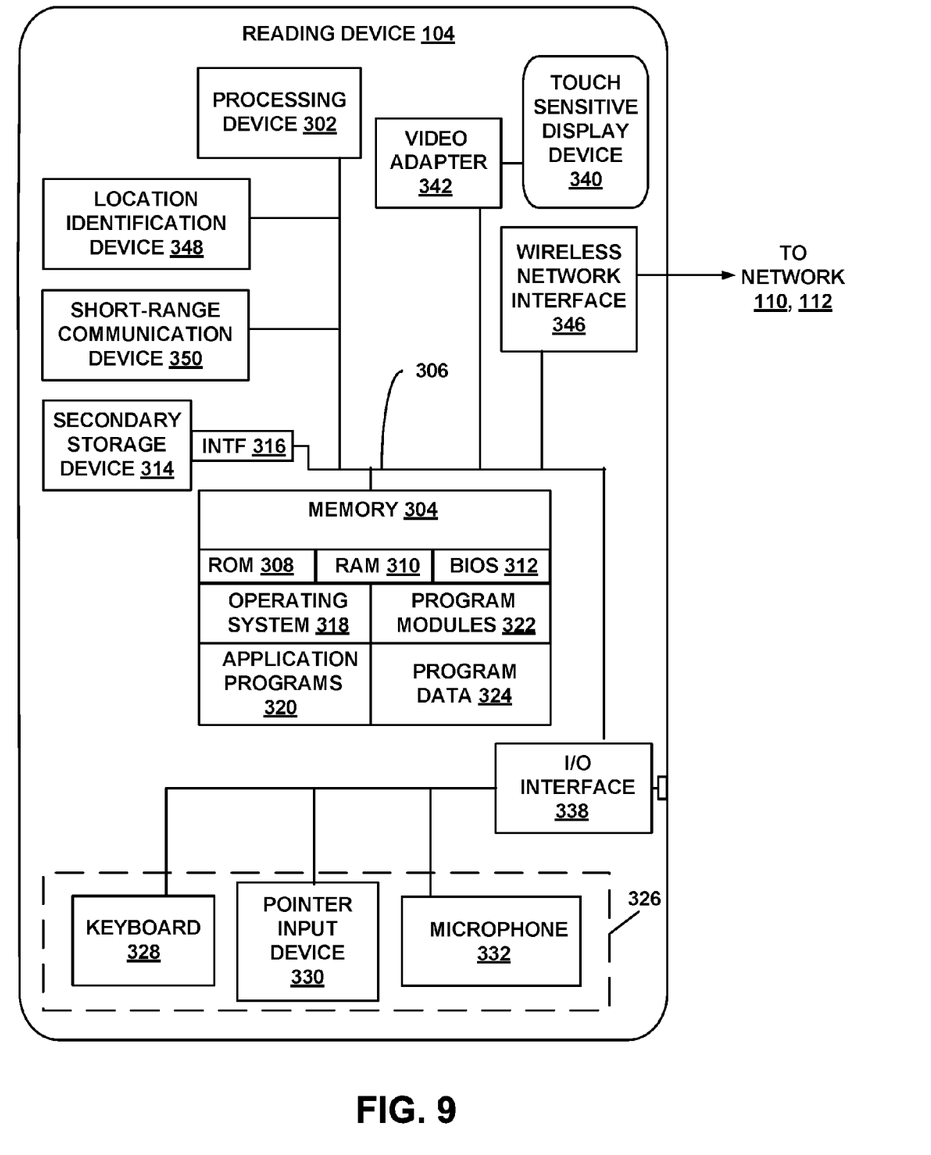
FIG. 9 illustrates an exemplary architecture of a reading device of the system of FIG. 1.

FIG. 9 illustrates an exemplary architecture of the reading device 104. The reading device 104 illustrated in FIG. 9 is used to execute the operating system, application programs, and software modules (including the software engines) described herein.

The reading device 104 is a computing device of various types. In some embodiments, the reading device 104 is a mobile computing device. Examples of the reading device 104 as a mobile computing device include a mobile device (e.g., a smart phone and a tablet computer), a wearable computer (e.g., a smartwatch and a head-mounted display), a personal digital assistant (PDA), a handheld game console, a portable media player, a ultra-mobile PC, a digital still camera, a digital video camera, and other mobile devices. In other embodiments, the reading device 104 is other computing devices, such as a desktop computer, a laptop computer, or other devices configured to process digital instructions.

It is recognized that the architecture illustrated in FIG. 9 can also be implemented in other computing devices used to achieve aspects of the present disclosure. For example, the data management system 106 can be configured similarly to the architecture of FIG. 9. To avoid undue repetition, this description of the reading device 104 will not be separately repeated herein for each of the other computing devices including the data management system 106.

The reading device 104 includes, in some embodiments, at least one processing device 302, such as a central processing unit (CPU). A variety of processing devices are available from a variety of manufacturers, for example, Intel or Advanced Micro Devices. In this example, the reading device 104 also includes a system memory 304, and a system bus 306 that couples various system components including the system memory 304 to the processing device 302. The system bus 306 is one of any number of types of bus structures including a memory bus, or memory controller; a peripheral bus; and a local bus using any of a variety of bus architectures.

The system memory 304 includes read only memory 308 and random access memory 310. A basic input/output system 312 containing the basic routines that act to transfer information within the reading device 104, such as during start up, is typically stored in the read only memory 308.

The reading device 104 also includes a secondary storage device 314 in some embodiments, such as a hard disk drive, for storing digital data. The secondary storage device 314 is connected to the system bus 306 by a secondary storage interface 316. The secondary storage devices and their associated computer readable media provide nonvolatile storage of computer readable instructions (including application programs and program modules), data structures, and other data for the reading device 104.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 314 or memory 304, including an operating system 318, one or more application programs 320, other program modules 322, and program data 324.

In some embodiments, the reading device 104 includes input devices to enable a user to provide inputs to the reading device 104. Examples of input devices 326 include a keyboard 328, a pointer input device 330, a microphone 332, and a touch sensitive display 340. Other embodiments include other input devices. The input devices are often connected to the processing device 302 through an input/output interface 338 that is coupled to the system bus 306. These input devices 326 can be connected by any number of input/output interfaces, such as a parallel port, serial port, game port, or a universal serial bus. Wireless communication between input devices and interface 338 is possible as well, and includes infrared, BLUETOOTH® wireless technology, 802.11a/b/g/n, cellular, or other radio frequency communication systems in some possible embodiments.

In this example embodiment, a touch sensitive display device 340 is also connected to the system bus 306 via an interface, such as a video adapter 342. The touch sensitive display device 340 includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the display device 340, the reading device 104 can include various other peripheral devices (not shown), such as speakers or a printer.

When used in a local area networking environment or a wide area networking environment (such as the Internet), the reading device 104 is typically connected to the network through a network interface, such as a wireless network interface 346. Other possible embodiments use other communication devices. For example, some embodiments of the reading device 104 include an Ethernet network interface, or a modem for communicating across the network.

The reading device 104 typically includes at least some form of computer-readable media. Computer readable media includes any available media that can be accessed by the reading device 104. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the reading device 104. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 9 is also an example of programmable electronics, which may include one or more such computing devices, and when multiple computing devices are included, such computing devices can be coupled together with a suitable data communication network so as to collectively perform the various functions, methods, or operations disclosed herein.

Referring again to FIG. 9, the reading device 104 can include a location identification device 348. The location identification device 348 is configured to identify the location or geolocation of the reading device 104. The location identification device 348 can use various types of geolocating or positioning systems, such as network-based systems, handset-based systems, SIM-based systems, Wi-Fi positioning systems, and hybrid positioning systems. Network-based systems utilize service provider's network infrastructure, such as cell tower triangulation. Handset-based systems typically use the Global Positioning System (GPS). Wi-Fi positioning systems can be used when GPS is inadequate due to various causes including multipath and signal blockage indoors. Hybrid positioning systems use a combination of network-based and handset-based technologies for location determination, such as Assisted GPS.

Referring again to FIG. 9, the reading device 104 further includes a short-range wireless communication device 350. The short-range wireless communication device 350 is configured to establish short-range wireless communication with the sensing patch 102. Short-range wireless communication is one-way or two-way short-range to medium-range wireless communication. Short-range wireless communication can be established according to various technologies and protocols. Examples of short-range wireless communication include a radio frequency identification (RFID), a near field communication (NFC), a Bluetooth technology, and a Wi-Fi technology.

The various examples and teachings described above are provided by way of illustration only and should not be construed to limit the scope of the present disclosure. Those skilled in the art will readily recognize various modifications and changes that may be made without following the example examples and applications illustrated and described herein, and without departing from the true spirit and scope of the present disclosure.

What is claimed is:

1. A physical assessment parameter sensing patch comprising:
   a first layer including an adhesive configured to be removably applied to a surface of a subject;
   a circuit fixed relative to the first layer and including a sensor unit and a communication unit, the sensor unit operable to detect one or more physical assessment parameters of the subject, and the communication unit configured to wirelessly communicate with a reading device;
   an antenna electrically connected to the communication unit and configured to receive and transmit a radio frequency signal, the antenna movably disposed within the sensing patch relative to the first layer; and
   an antenna enclosure fixed relative to the first layer and configured to movably receive the antenna therein such that the antenna is movable within the antenna enclosure as the first layer deforms;
   wherein the antenna is connected at an anchor point within the antenna enclosure, and the antenna is adapted to float freely within the antenna enclosure relative to the anchor point; and
   wherein the antenna is made from etched metal foil.

2. The sensing patch of claim 1, further comprising a second layer cooperating with the first layer to house the circuit and the antenna enclosure between the first and second layers.

3. The sensing patch of claim 1, wherein the antenna enclosure includes a wire hole through which electrical wires pass, the electrical wires electrically connecting the circuit and the antenna.

4. The sensing patch of claim 1, wherein the first layer is made of a flexible material.

5. The sensing patch of claim 1, wherein the circuit is made of a flexible printed circuit board.

6. The sensing patch of claim 1, wherein the sensor unit includes a thermistor.

7. The sensing patch of claim 1, wherein the sensing patch is sized to be unswallowable.

8. The sensing patch of claim 1, wherein the circuit is configured to communicate with the reading device via short-range communication.

9. The sensing patch of claim 8, wherein the short-range communication includes near field communication (NFC).

10. The sensing patch of claim 8, wherein the circuit is configured as a passive device.

11. The sensing patch of claim 1, further comprising a second layer cooperating with the first layer to define a space within which the antenna moves relative to the first and second layers.

12. A system for detecting a physical assessment parameter of a subject, the system comprising:
 a sensing patch including:
  a first layer including an adhesive configured to be removably applied to a surface of the subject;
  a circuit fixed relative to the first layer and including a sensor unit, the sensor unit operable to detect one or more physical assessment parameters of the subject;
  an antenna electrically connected to the circuit and configured to receive and transmit a radio frequency signal, the antenna movably disposed within the sensing patch relative to the first layer; and
  an antenna enclosure fixed relative to the first layer and configured to movably receive the antenna therein such that the antenna is movable within the antenna enclosure as the first layer deforms;
  wherein the antenna is connected at an anchor point within the antenna enclosure, and the antenna is adapted to float freely within the antenna enclosure relative to the anchor point; and
  wherein the antenna is made from etched metal foil; and
 a reading device configured to communicate with the sensing patch and receive the one or more physical assessment parameters from the sensing patch.

13. The system of claim 12, wherein the sensing patch and the reading device are configured to be connected via short-range communication.

14. The system of claim 12, wherein the sensing patch is configured as a passive device, and the reading device is configured to produce electromagnetic induction to power the sensing patch when the reading device are located within a read range of the sensing patch.

15. The system of claim 12, wherein the first layer of the sensing patch is made of a flexible material.

16. A physical assessment parameter sensing patch comprising:
 a first layer including an adhesive configured to be removably applied to a surface of a subject;
 a circuit fixed relative to the first layer and including a sensor unit and a communication unit, the sensor unit operable to detect one or more physical assessment parameters of the subject, and the communication unit configured to wirelessly communicate with a reading device;
 an antenna electrically connected to the communication unit and configured to receive and transmit a radio frequency signal, the antenna movably disposed within the sensing patch relative to the first layer; and
 an antenna enclosure fixed relative to the first layer and configured to movably receive the antenna therein such that the antenna is movable within the antenna enclosure as the first layer deforms;
 wherein the antenna is connected at an anchor point within the antenna enclosure, and the antenna is adapted to float freely within the antenna enclosure relative to the anchor point; and
 wherein the sensing patch includes a coating providing an undesirable taste to prevent swallowing.

* * * * *